United States Patent [19]

Noolandi

[11] Patent Number: 5,167,784
[45] Date of Patent: Dec. 1, 1992

[54] SEQUENCING LARGE NUCLEIC ACID FRAGMENTS

[75] Inventor: Jaan Noolandi, Mississauga, Canada

[73] Assignee: Xerox Corporation, Stamford, Conn.

[21] Appl. No.: 754,854

[22] Filed: Sep. 4, 1991

[51] Int. Cl.⁵ .................. G01N 27/26; B01D 57/02
[52] U.S. Cl. ........................ 204/182.8; 204/299 R
[58] Field of Search ............ 204/182.8, 299 R, 180.1

[56] References Cited

U.S. PATENT DOCUMENTS

| | | | |
|---|---|---|---|
| 4,473,452 | 9/1984 | Cantor et al. | 204/180 |
| 4,663,015 | 5/1987 | Sleeter et al. | 204/299 R |
| 4,666,581 | 5/1987 | Itoh et al. | 204/299 R |
| 4,729,947 | 3/1988 | Middendorf et al. | 435/6 |
| 4,737,251 | 4/1988 | Carle et al. | 204/182.2 |
| 4,740,283 | 4/1988 | Laas et al. | 204/182.8 |
| 4,865,968 | 9/1989 | Orgel et al. | 435/6 |
| 4,870,004 | 9/1989 | Conroy et al. | 435/6 |
| 4,892,638 | 1/1990 | Watanabe et al. | 204/299 R |
| 4,904,366 | 2/1990 | Tokita et al. | 204/299 R |
| 4,911,817 | 3/1990 | Kindlmann | 204/299 R |
| 4,959,133 | 9/1990 | Adcock | 204/182.8 |
| 4,971,671 | 11/1990 | Slater et al. | 204/180.1 |

OTHER PUBLICATIONS

E. Lai et al., "Effects of Electric Field Switching on the Electrophoretic Mobility of Single Stranded DNA Molecules in Polyacrylamide Gels"; Electrophoresis, 1989, pp. 65-75.

Carle, "Electrophoretic Separations of Large DNA Molecules of Periodic Inversion of the Electric Field"; Science; 232; Apr. '86; pp. 65-68.

Turmel, "High Resolution Zero Integrated Field Electrophoresis of DNA"; Electrophoresis of Large DNA Molecules: Theory & Applications; Cold Harbor Lab Press; 1990, pp. 101-131.

Primary Examiner—John Niebling
Assistant Examiner—John S. Starsiak, Jr.
Attorney, Agent, or Firm—Oliff & Berridge

[57] ABSTRACT

The base sequence of large single stranded nucleic acids is determined by retarding the migration rate of a nucleic acid fragment of n bases below a migration rate which would otherwise be the same as the migration rate of a nucleic acid fragment of n bases in a polyacrylamide gel under continuous field gel electrophoresis. A plurality of sequences of electric field pulses is applied to the gel in one dimension.

25 Claims, 7 Drawing Sheets

SEQUENCING LARGE NUCLEIC ACID FRAGMENTS

1. FIELD OF THE INVENTION

The present invention is directed to methods of sequencing single stranded nucleic acid molecules on polyacrylamide gels using gel electrophoresis and more particularly to such methods using pulsed field gel electrophoresis.

2. Background

Recently, advances in DNA and RNA research have led to many new and improved strategies for determining the nucleotide base sequence of these acids. In addition to cloning, polymerase chain reaction and enzymatic sequencing protocols, gel electrophoresis plays an important part in sequencing methods. This has created a demand for more rapid gel electrophoretic methods as well as methods having increased resolution. Unfortunately, gel electrophoretic techniques which use continuous electric fields up to at least 100 Volts per centimeter in a uniform gel (polyacrylamide) result in a loss of resolution on the gel between similar length fragments greater than about 300 bases. This is a severe limitation, increasing the number of subcloning steps as the gene must be cut many times into small fragments in order to determine the base sequence, and information about the structure of the entire gene is lost or becomes difficult to obtain.

Several attempts have been made to increase the band resolution of electrophoretic methods for separating large duplex DNA molecules in agarose gels. For example, U.S. Pat. No. 4,473,452 to Cantor et al. teaches the use of transverse electric fields which alternate between low and high intensities. This protocol allows the separation of larger size fragments of double stranded DNA in agarose gels at a higher speed and resolution. U.S. Pat. No. 4,740,283 to Laas et al. teaches a pulsed field gradient gel electrophoretic apparatus wherein the electrodes are oriented to provide a three-dimensional field across the face of the gel rather than in the plane of the gel. As a result, the molecules from the gel proceed down their respective lanes in a sawtooth matter. Both the '452 and '283 electrophoretic methods are inconvenient because they cannot be run on conventional electrophoretic equipment due to the requirement of special electrode configurations. Moreover, their use in sequencing protocols is unclear.

U.S. Pat. No. 4,737,251 to Carle et al. teaches an electrophoretic method for separating large molecular weight DNAs in agarose gel wherein the electric field is periodically inverted essentially in one dimension. A higher voltage or longer time is used in one direction than in the other. This method is thus used for separating large molecular weight DNAs wherein exceptional resolution is not necessary, using time intervals for field duration which range from seconds to hours.

In an effort to increase resolution in gel electrophoresis for sequencing single stranded DNA molecules, Tokita et al. in U.S. Pat. No. 4,904,366 teach lowering the ionic strength of the buffer solution in the polyacrylamide gel near the detector on a DNA base sequencer. The electric field intensity near the detector is thus increased, resulting in a higher migration speed and enhancing the resolving power of the apparatus. The loss of band resolution between large single stranded DNA fragments is thought to be caused by a phenomenon relating to the alignment of large molecules (larger than gel pore size) in the electric field which affects the migration patterns of the large sized fragments in the polyacrylamide gel rather than being directly related to the pH of the gel.

In a constant electric field, nucleic acid fragments containing up to about 300 bases migrate at a rate which is inversely proportional to their base content number, i.e., a fragment of $n+1$ base length migrates slower than one which is n bases long, which in turn migrates slower than one of $n-1$ bases, etc. As a result of this phenomenon, the bands of nucleic acid on a polyacrylamide sequencing gel are "compressed", having no discernable resolution between nucleic acid fragments having successively longer base lengths. In automated sequencers, currently being used in the Human Genome program, the bands which indicate the arrival of a particular base at the bottom of a gel are broadened for a number of reasons, resulting in poor resolution between them on a chart recorder. Referring to FIG. 1 a schematic of a chart recorder printout, bands 30, 31, 32, 33 and 34, corresponding to the same number of bases in a nucleic acid fragment are easily resolved. In contrast, bands 400, 401, 402, 403, and 404 show very poor resolution between them. Prior art approaches to overcoming this limitation of resolution have involved the use of pulsed fields with limited success.

For example, Lai et al. in "Effect of electric field switching on the electrophoretic mobility of single-stranded DNA molecules in polyacrylamide gels", *Electrophoresis*, 10, 65-70, 1989, discuss the application of field inversion gel electrophoresis to single stranded DNA molecules having a base length greater than 130. The migration rate of DNA molecules larger than 130 bases was shown to be retarded as compared to their migration rates in conventional and unidirectional pulsed gels. The application of the Lai et al. method, however, failed to retard the migration of nucleic acid fragments larger than 600 bases long. While retarding the migration rate of fragments 130 bases long is certainly of interest, it is, however, somewhat inconsequential. At a length of 130 bases, using conventional electrophoretic techniques, nucleic acid fragments migrate through the gel at a rate which is inversely proportional to their base length and hence produce satisfactory band resolution on the gel. Therefore, methods which resolve single stranded DNA fragments of higher base lengths, the fragments of which would otherwise migrate at a rate the same as a fragment using constant field electrophoresis, are still needed.

SUMMARY OF THE INVENTION

The present invention pertains to a method of determining the base sequence of large single stranded nucleic acid fragments using gel electrophoresis. The method comprises retarding the migration rate of a nucleic acid fragment of n bases below a migration rate which would otherwise be the same as the migration rate of a nucleic acid fragment of n bases in a polyacrylamide gel under continuous field gel electrophoresis. A plurality of sequences of electric field pulses is applied in one dimension to the gel. Each of the sequences is comprised of a first pulse of a positive magnitude, applied for a first time period, and a second pulse of a negative magnitude applied for a second time period. The method is especially useful in sequencing long nucleic acid fragments, especially those which are longer than 300 bases and preferably longer than 600 bases.

BRIEF DESCRIPTION OF THE DRAWINGS

A more complete understanding of the present invention can be obtained by reference to the accompanying drawings wherein.

DETAILED DESCRIPTION OF PREFERRED EMBODIMENTS

Figure 1:
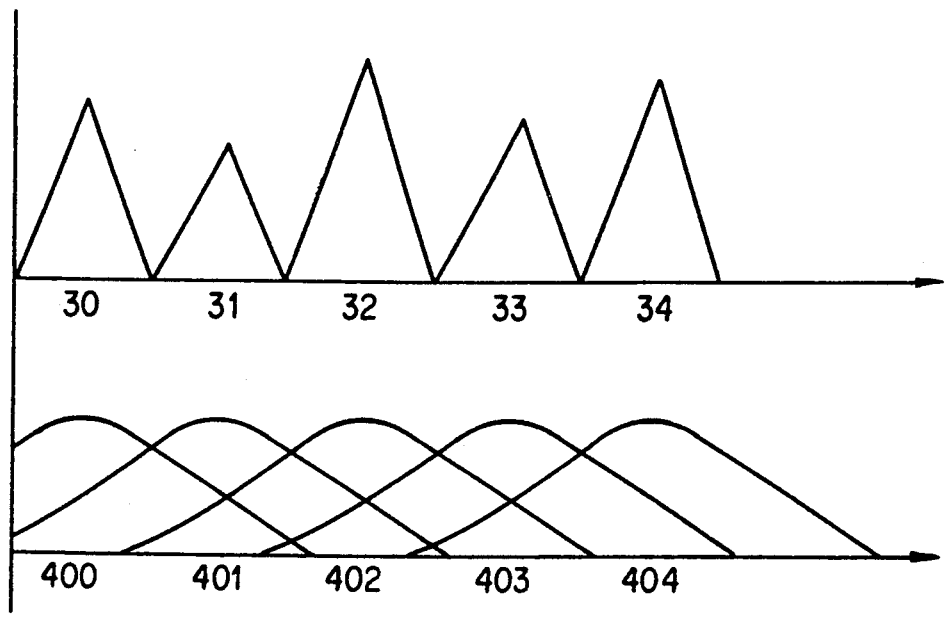
FIG. 1 shows schematic fluorescence data obtained on an automatic sequencer for relatively low fragment lengths, and broadening for higher fragment lengths using prior art methods.

In preparation for the method of the present invention, single stranded nucleic acids, as for example, DNA, can be prepared for sequencing prior to electrophoresis by any of the methods known in the art, for example, the Maxam and Gilbert chemical method or the Sanger, Nicklaus and Coulsen enzymatic method (Sambrook, Maniatis and Frisch, *Molecular Cloning: A Laboratory Manual*, Cold Spring Harbor Laboratory (1989). An electrophoretic gel is prepared from polyacrylamide or an equivalent gel and the nucleic acid fragments are deposited on the gel in a conventional manner (e.g., 4 wells at the upper edge of the gel, each corresponding to one of the 4 bases). An automated sequencer (e.g., Pharmacia, duPont, Applied Systems) in which the flourescently labeled DNA fragments migrating down the gel are detected at the bottom by emitting a signal which is recorded on a chart recorder can be used. Alternatively, the method of the present invention can be used with more conventional sequencing methods wherein the sequence of the DNA is read directly off of the gel. Both methods will be immediately recognized by those skilled in the art.

By applying a plurality of sequences of electric field pulses in one dimension to the gel, the migration rate of nucleic acid fragments, as for example DNA and RNA fragments, containing n bases is retarded below a rate which would otherwise be the same as the migration rate of a nucleic acid fragment of n bases in a polyacrylamide gel under a constant electric field. Although the details of the molecular mechanism which governs the retardation of migration rates is quite complicated, in summary, during the time involved in which the negative pulse is applied, there is a backward displacement of the fragments on the gel. If the time period is long enough to allow a fragment of n bases to relax to the negative field pulse, the net displacement of the fragment with n+1 bases is less than, and hence its migration rate retarded below, the net displacement of a fragment with n bases. Each of the sequences is comprised of a first pulse of a positive magnitude which is applied for a given time, and a second pulse of a negative magnitude which is applied for a given time.

The present invention, due to its migration retarding effect, is therefore useful in sequencing nucleic acid fragments having a length greater than 300 bases, preferably greater than 400 bases and most preferably greater than 600 bases. To sequence base lengths lower than this, conventional constant field electrophoresis is usually quite effective. Thus a constant field may be applied until the sequencing reaches these ranges, at which time application of a plurality of sequences of electric pulses to the gel is employed. There is theoretically no limit to the upper number of bases between which the present invention can resolve and hence sequence. However, present sequencing methods can only synthesize fragments of nucleic acids up to about 2Kb using available polymerases. More polymerases will be needed before sequencing can approach these ranges, but upon their development the present invention would permit resolution of fragments of such lengths.

Figure 2:
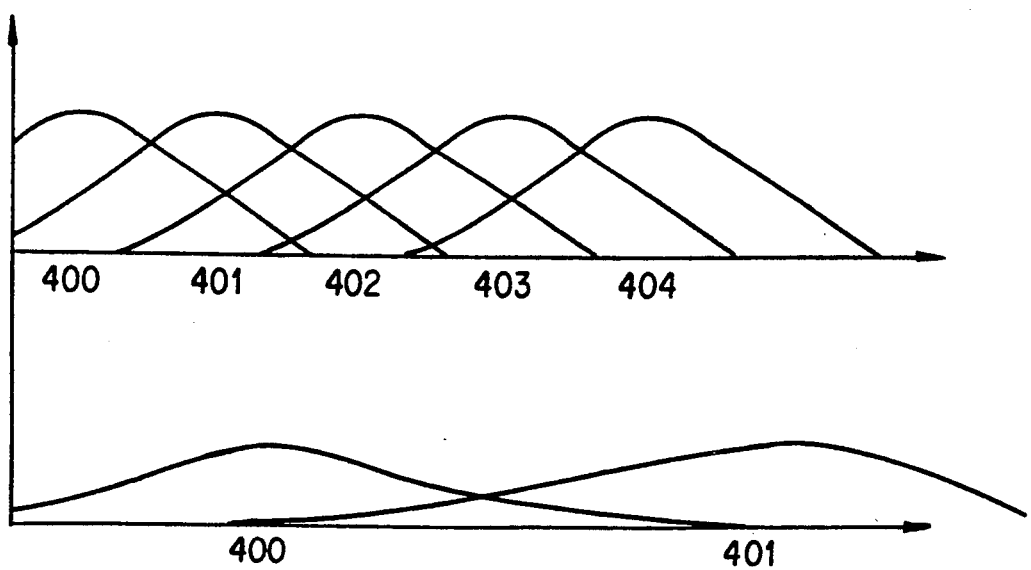
FIG. 2 shows a comparison between the prior art and the present invention for schematic fluorescence data obtained for higher fragment lengths.

The retarded migration rates result in bands of nucleic acid fragments on the gel being "decompressed", thereby increasing the number of readable DNA fragments and hence readable bases per gel. With an automated sequencer the retarded migration rate results in bands on the chart recorder being spatially separated so as to facilitate nucleic acid base sequence reading. Reference is made to FIG. 2 wherein improved resolution between bands on a chart recorder is illustrated as a result of the present invention. Chart recorder sequence data for constant field electrophoresis is shown on the top line for nucleic acid fragments 400–404 bases in length. Resolution between bands of successively higher base length are poorly resolved because of the width of the bands. In contrast, the bottom line shows markedly increased resolution between nucleic acid fragments of 400 and 401 bases in length when the methods of the present invention are employed. The improved resolution is a direct result of the retarded migration rates obtained with the present invention. Essentially, the lower the time interval between successive signal detections on the recorder.

According to the present invention, the duration of at least one of the first time period $(T_1)$ and the second time period $(T_2)$ is from about 100 microseconds to about 10 milliseconds, preferably from about 1 millisecond to about 5 milliseconds and more preferably from about 2 milliseconds to about 4 milliseconds. The absolute value of at least one of the first voltage $(V_1)$ and the second voltage ($V_2$) is greater than zero and less than 10,000 Volts, preferably from about 300 to about 5000 Volts. In a preferred embodiment, the absolute value of the first voltage $V_1$ is greater than or equal to the absolute value of the second voltage $V_2$.

In one preferred embodiment, the value of the product of the first time period and the first voltage of a positive magnitude plus the value of the product of the second time period and the second voltage of negative magnitude divided by the sum of the first and the second time periods is essentially zero. Essentially zero is intended to mean that the average electric field as applied throughout the duration of the sequence is at or near zero. For example, if a sequence was comprised of a first pulse applied at +2000V for 1 millisecond and a second pulse was applied at −1000V for 2 milliseconds, the average electric field would be zero. Alternatively, if the value of the product of the first time period and the first voltage of a positive magnitude plus the value of the product of the second time period and the second voltage of negative magnitude divided by the sum of the first and the second time periods is less than about 50% of the larger of the first and second voltages, it can be considered to be essentially zero.

A DC power source having an available voltage range of +10,000 to −10,000 Volts and a slew rate of 200–500 Volts/microsec. may be used to provide the sequences of electric field pulses to the gel. Slew rate is used according to its known meaning in the art and is defined as the rate of voltage change/time or dV/dt. A timer/switcher capable of switching voltage in the order of microseconds should be used to control the power source.

In further embodiments, the method according to the present invention further comprises another step of repeating the plurality of sequences or a method wherein at least one of the first pulse and the second pulse in the sequence of pulses is comprised of a number of subpulses. Subpulses are pulses of a reverse voltage magnitude or zero which go back to the original magnitude at least once before the application of another subpulse of reverse magnitude. The duration of the inversion is in the order of microseconds. Subpulses are responsible for what is referred to as a shaking effect, helping the nucleic acid fragments move through the pores of the gel.

The following examples are illustrative in nature and are not intended to limit the scope of the invention in any way. Other equivalent methods of practicing the present invention may occur to those skilled in the art upon reading the present specification.

EXAMPLES

Methods and Materials

Gel solutions are prepared by mixing together 7M urea (21g, ICN Biochemicals), acrylamide in a stock solution of acrylamide-N,N-methylene-bis-acrylamide (38:2 Broad) to a final acrylamide concentration of 4%, 6%, 8% and 12% respectively, and water to a total volume of 50 ml. TBE buffer (0.9 molar trisbase, 0.9 molar boric acid, 20 millimolar EDTA) is added to a final concentration of buffer between 0.5 and 1.5X using a stock solution 10X concentrated. Ammonium persulfate (0.07 to 0.8% weight volume) and N,N,N,tetra-methylethylene diamine (TEMED) (0.087 to 0.04% weight per volume) are added, amount dependent on the acrylamide concentration.

The gel solution is poured between a glass plate and a thermostatic plate (Pharmacia LKB) (550 millimeters by 220 millimeters) separated by 0.2 millimeters. The two plates are treated respectively by binding a repellant silane (Pharmacia LKB). The gel solution is allowed to polymerize for thirty minutes. Electrophoresis is carried out with the 2010 MACRO FOUR unit (Pharmacia LKB) using the same electrode buffer concentration as in the gel. Each gel is prerun at 2000 Volts constant voltage for two hours at 50° C. to reach a constant current plateau value. DNA from the bacterial phage M13 MP18 (Pharmacia LKB) is used as a standard marker and the radio labeled $^{35}S$ product of the dideoxy sequencing reaction using the T7 bacterial phage DNA fragments is prepared using a standard sequencing kit (Pharmacia LKB).

Relative mobility of the DNA fragments is calculated according to the distance in millimeters that a fragment of a given length migrated down the gel in relation to a fragment of 80, 90 or 100 bases long according to the formula:

$$\frac{\text{distance (mm) fragment of } n \text{ bases migrated}}{\text{distance (mm) fragment of 80, 90, or 100 bases migrated}}$$

The relative mobilities, as well as the actual distances in millimeters traveled by the fragments on the gel are reported in tables I–X corresponding to examples 1–10 below. Reported voltages are applied across the entire length of the gel (550 mm).

Comparative Example 1

Figure 3:
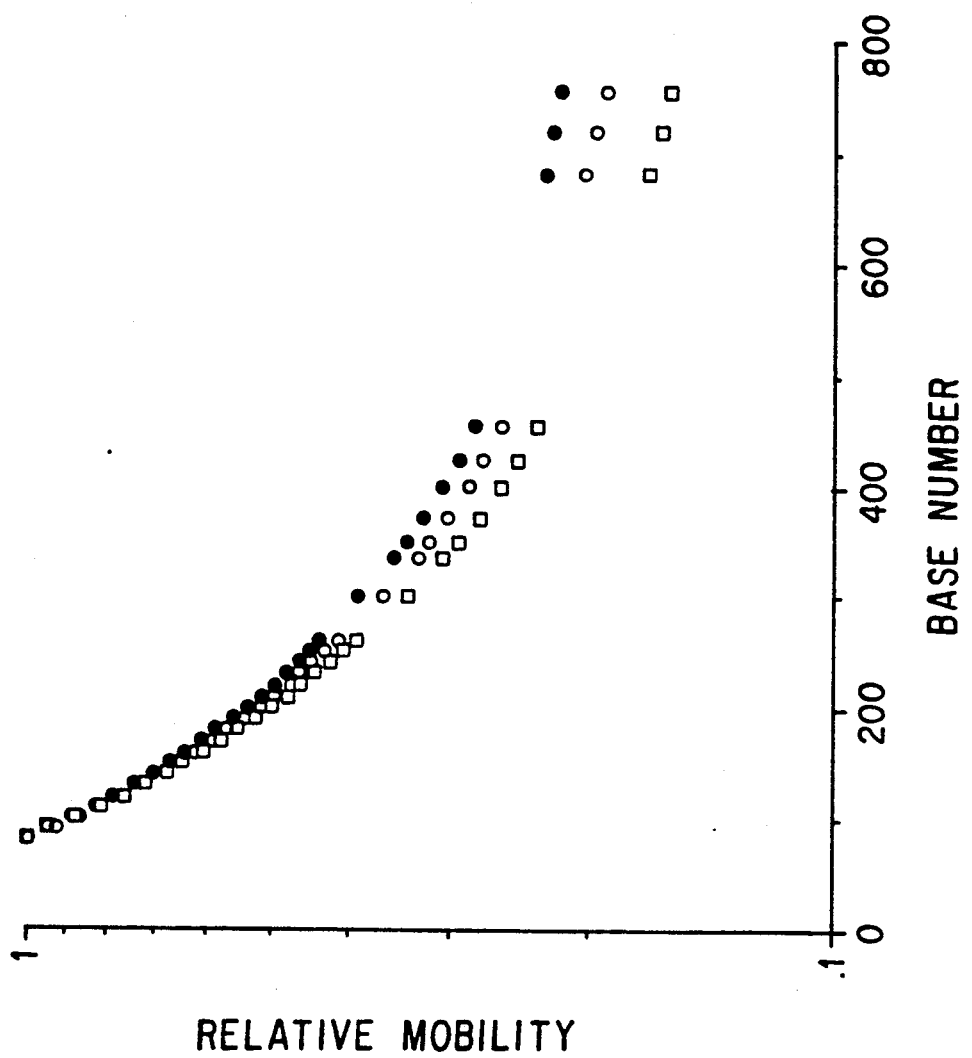
FIG. 3 shows the effect of the ionic strength (TBE conc.) of the gel on the relative electrophoretic mobility of DNA fragments (1X TBE, ○; 0.5X TBE, ●; 1.5X TBE, □ ).

Electrophoresis is run at a constant electric field of 2000V in a 6% polyacrylamide gel. The ionic strength of the gel is varied from 0.5X to 1.5X TBE. The run is stopped when the dye marker control xylene cyanol reached the bottom of the gel. Relative mobilities of DNA fragments as compared to an 80 base fragment are recorded and are reported in Table I. The overall effect of varying the ionic strength on the relative mobilities of the fragments is seen in FIG. 3.

Comparative Example 2

Figure 4:
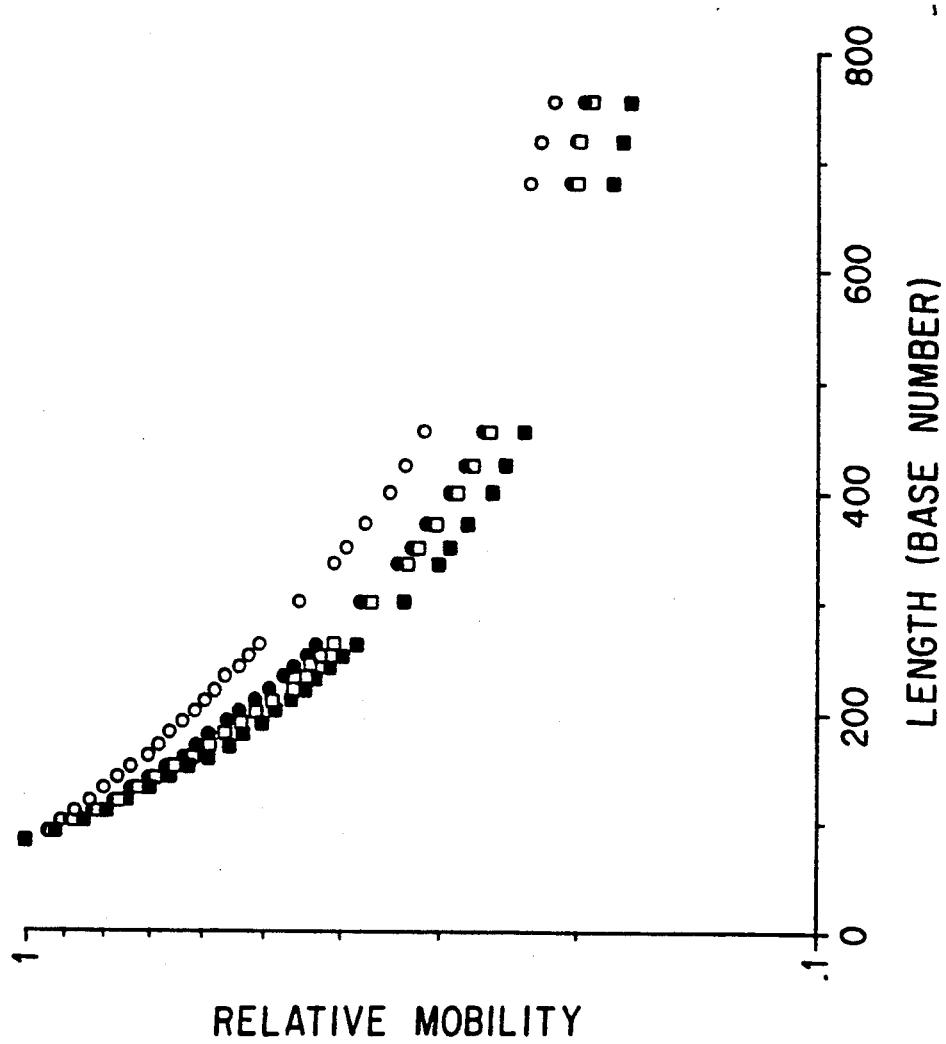
FIG. 4 shows the effect of the polyacrylamide gel concentration; (4%, ○; 6% ●; 8%; □; 12%, ■) on the relative mobility of single stranded DNA fragments ranging in length from 80 to 755 bases at a constant of 2000 Volts.

Electrophoresis is run at a constant electric field of 2000V and a constant ionic strength of 1X TBE in 4%, 6%, 8% and 12% acrylamide gels. The experiment is stopped when the dye marker control (xylene cyanol) reaches the bottom of the gel. The relative mobility of the fragments compared to an 80 base fragment are reported in Table II. The effect of acrylamide concentration is illustrated in FIG. 4.

Comparative Example 3

Figure 5:
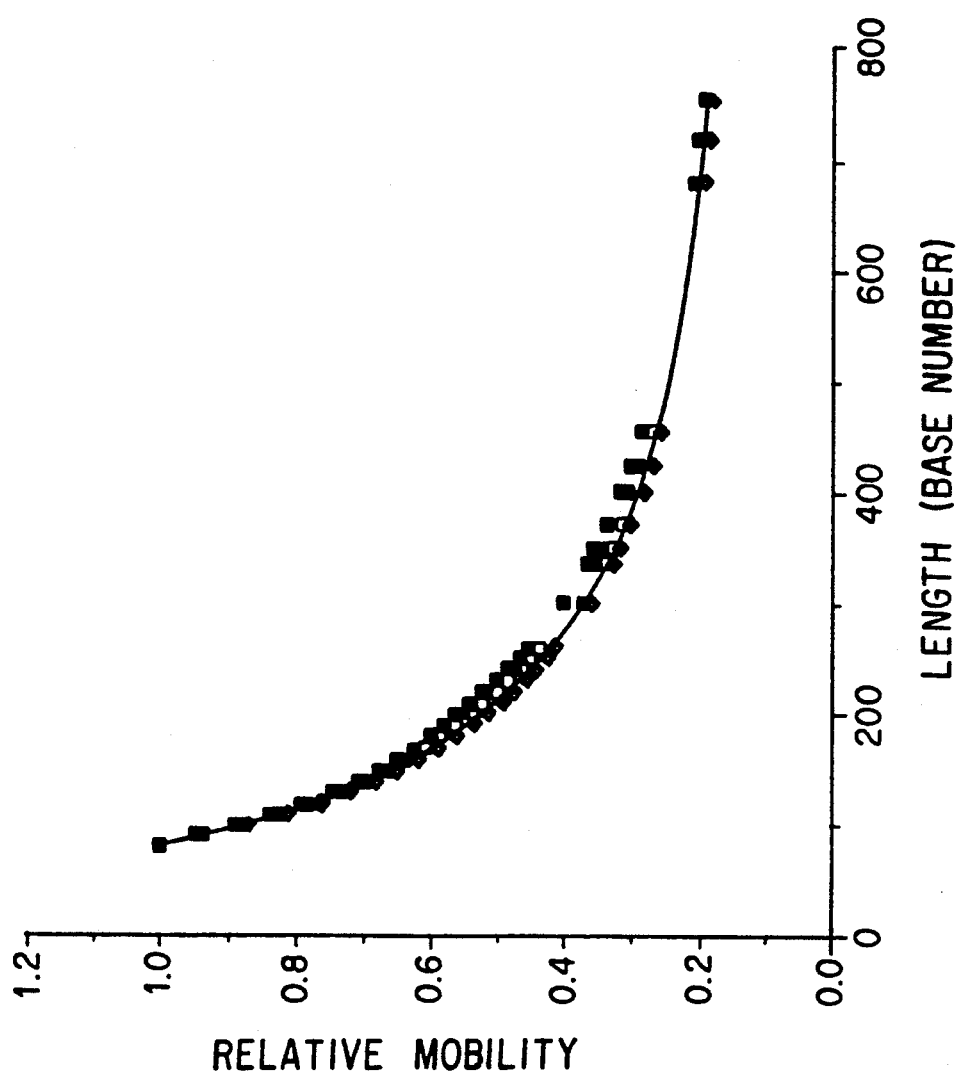
FIG. 5 shows the effect of temperature on the relative electrophoretic mobility of DNA fragments. (55° C., □; 45° C., ●; 40° C., ■; 35° C., ○; 30° C., □,)

Electrophoresis is run at a constant electric field of 2000V in 6% acrylamide gel at ionic strength of 1X TBE at the temperatures of 55° C., 45° C., 40° C., 35° C. and 30° C. Relative mobility compared to an 80 base fragment is reported in Table III. The effect of temperature variation on the relative mobility is illustrated in FIG. 5.

Comparative Example 4

Figure 6:
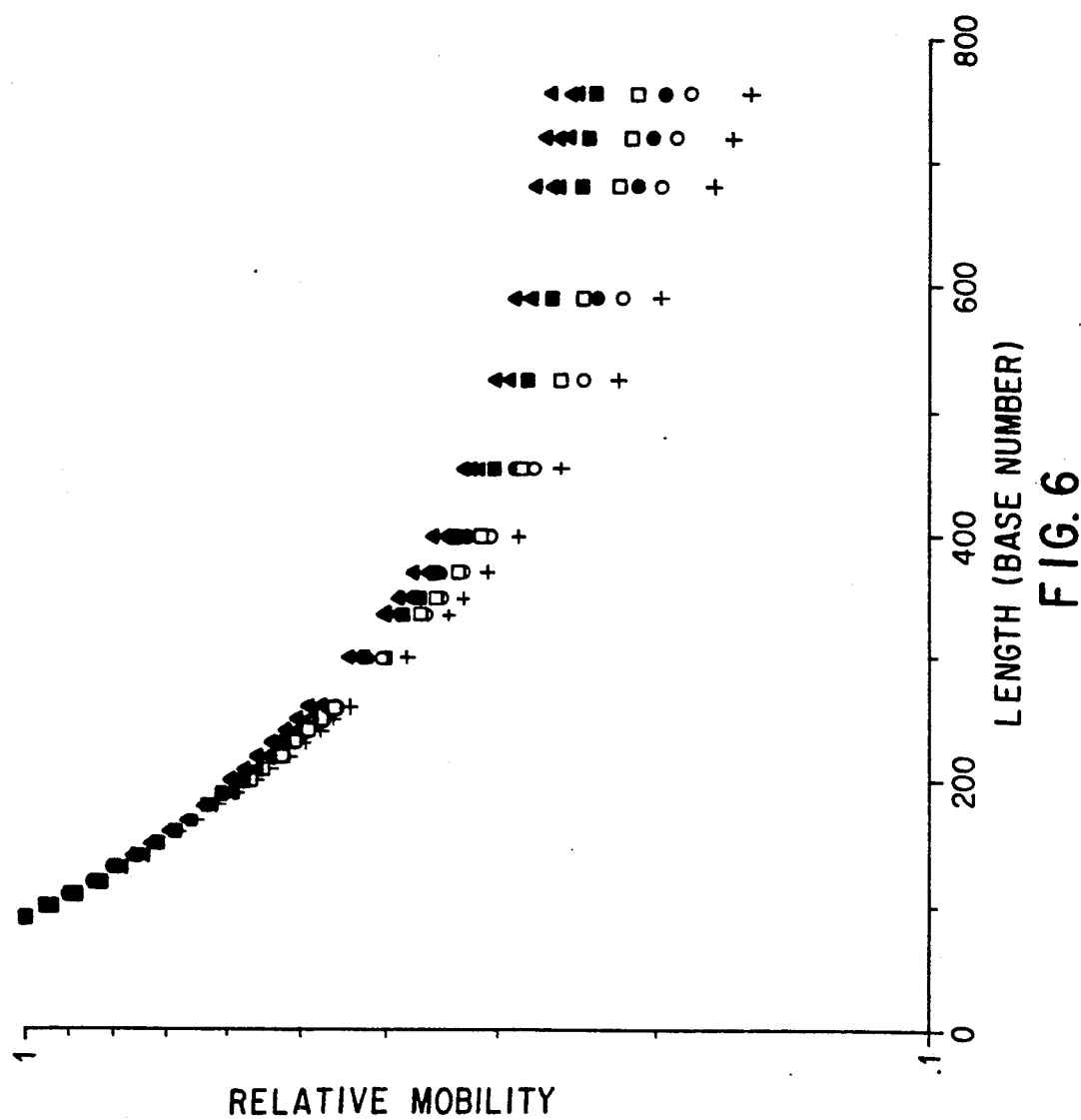
FIG. 6 shows the effect of field strength on the relative electrophoretic mobility of DNA fragments. (750V, +; 1000V, ○; 1500V, ●; 2000V, □, 2500V; ■; 3000V, △; 4000V, ▲; 5000V ▲)

Electrophoresis is run in 6% acrylamide gel at an ionic strength of 1X TBE, at a temperature of 50° C. at constant electric field strengths of 750 Volts, 1000 Volts, 1500 Volts, 2000 Volts, 2500 Volts, 3000 Volts, 4000 Volts and 5000 Volts. The relative mobility of the fragments as compared to a 90 base fragment is reported in Table IV. The effect of field strength on the relative mobilities of the fragments is illustrated in FIG. 6.

Comparative Example 5

Figure 7:
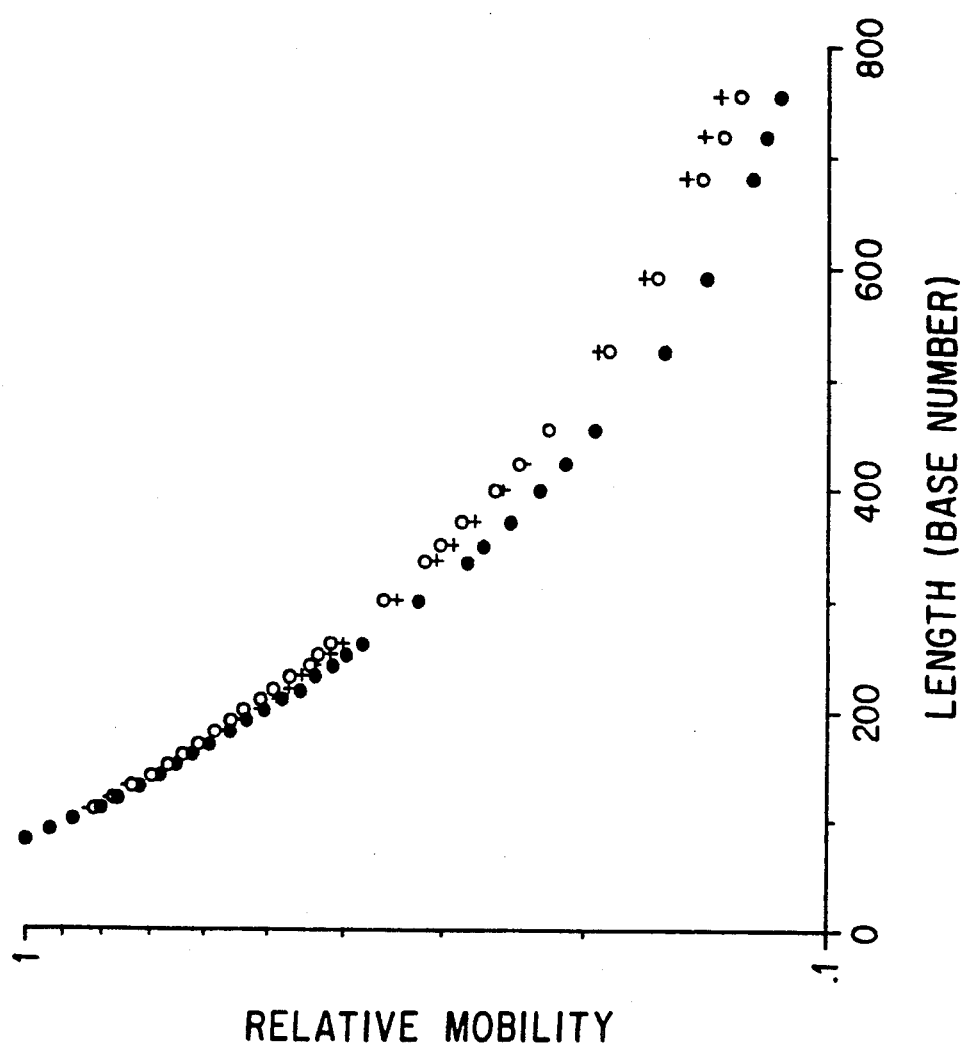
FIG. 7 shows the effect of intermittent field pulsing on the relative electrophoretic mobility of single stranded DNA fragments compared to the mobility with a continuous field of the same intensity. (1000V, +; 1s, 1000V and 2s, 0V, ○; 1s, 1000V and 5s, 0V, ●)

Electrophoresis is run in 6% acrylamide gel at an ionic strength of 1X TBE and a temperature of 50° C. The buffer is changed daily. A constant electric field of 1000 Volts is applied for eight hours, followed by a sequence of pulses of 1 second at 1000 Volts and 2 seconds at zero Volts, followed by a sequence of 1 second at 1000 Volts and 5 seconds at zero Volts, followed by 1 seconds at 1000 Volts and 1 seconds at zero Volts. The relative mobility of the fragments as compared to an 80 base length fragment is reported in Table V. The effect of this "intermittent" field on the relative mobilities is illustrated by FIG. 7.

Example 6

Figure 8:
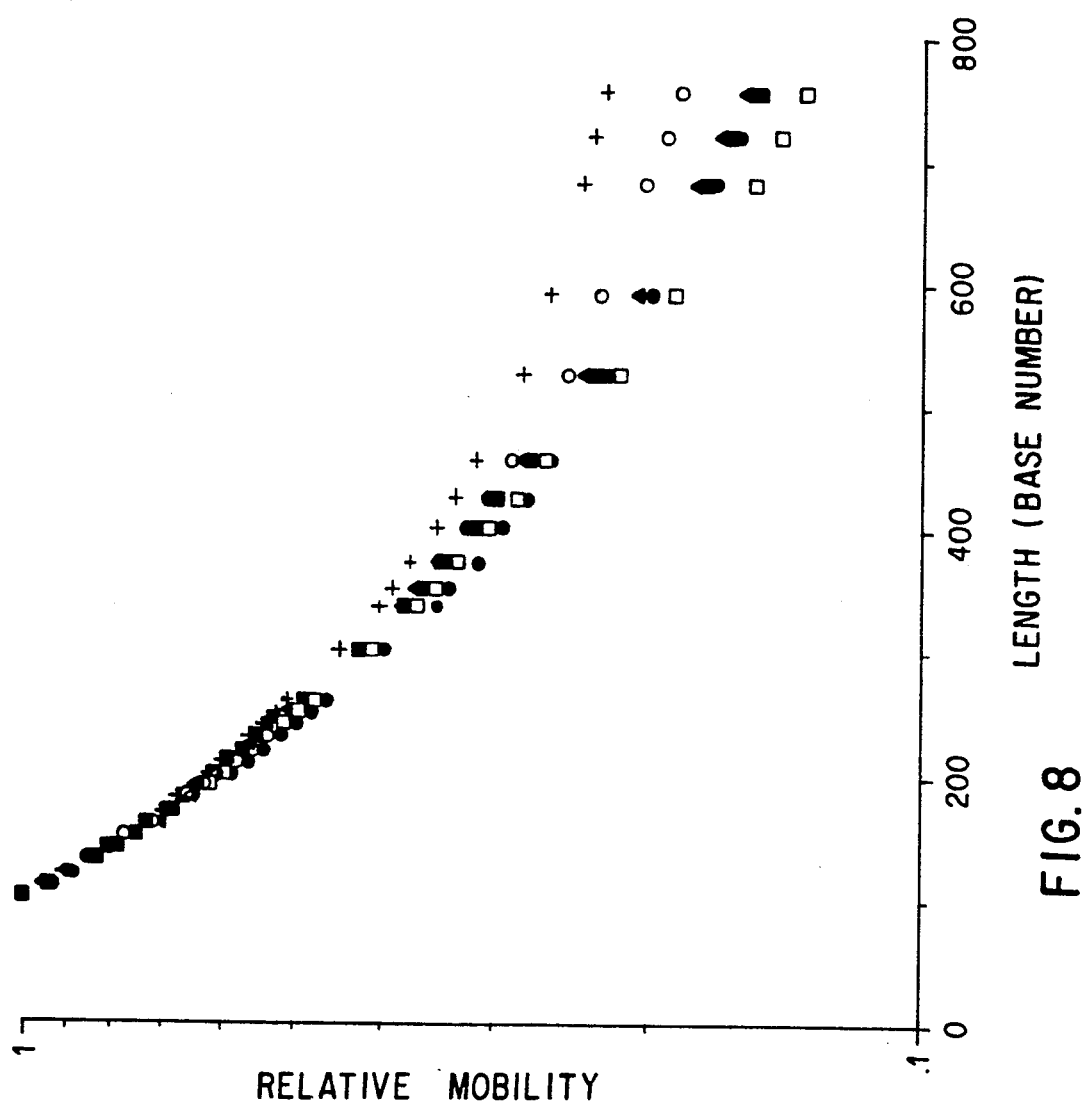
FIG. 8 shows the effect of pulse sequences according to an embodiment of the present invention compared to a continuous field of the same intensity on the relative electrophoretic mobility of DNA fragments. (2000V +; 1 ms, 2000V and 1ms, −300V, ○; 1ms, 2000V and 1ms, −620V, ●; 2ms, 2000V and 4ms, −630V, □; 2ms, 2000V and 2ms, −1000V ■; 2ms, 2000V, 1ms, −200V, △)

Electrophoresis is run in 6% acrylamide gel having an ionic strength of 1X TBE at a temperature of 50° C. A continuous electric field of 2000 Volts is run for 4.4 hours. This is followed in several runs using the following pulsed sequences: sequence of 1 millisecond at 2000 Volts and 1 millisecond at −300 Volts; a sequence of 1 millisecond at 2000 Volts and 1 millisecond at −620 Volts; a sequence of 2 milliseconds at 2000 Volts and 4 milliseconds at −630 Volts; a sequence of 2 milliseconds at 2000 Volts and 2 milliseconds at −1000 Volts; a sequence of 2 milliseconds at 2000 Volts and 1 millisecond at −2000 Volts. The relative mobility of the fragments to a 100 base length fragment is reported in Table VI. FIG. 8 illustrates the effect of these pulsed sequences on the relative mobility of the fragments.

Example 7

Electrophoresis is run in 6% acrylamide gel having an ionic strength of 1X TBE at a temperature of 50° C. A continuous electric field of 2000 Volts is applied for 4.4 hours. This is followed by a sequence of pulses of millisecond at 2000 Volts and 1 millisecond at −300 Volts; a sequence of 2 milliseconds at 2000 Volts; and 2 milliseconds at −300 Volts; a sequence of 2 milliseconds at 2000 Volts and 4 milliseconds at −300 Volts. The relative mobility of the fragments to a 100 base length fragment is reported in Table VII.

Example 8

Electrophoresis is run in 6% acrylamide gel having an ionic strength of 1X TBE at a temperature of 50° C. A continuous electric field of 2000 Volts is applied for 4 hours. This is followed in several runs using the following pulse sequences: sequence of 1 second at 2000 Volts alternating with 1 second at −620 Volts; a sequence of 10 milliseconds at 2000 Volts alternating with 10 milliseconds at −620 Volts; a sequence of 5 millisecond at 2000 Volts alternating with 5 milliseconds at −620 Volts; a sequence of 2 millisecond at 2000 Volts alternating with 2 milliseconds at −620 Volts; and finally a sequence of 1 millisecond at 2000 Volts alternating with 1 millisecond at −620 Volts. The relative mobility of the fragments as compared to 100 base length fragment is reported in Table VIII.

Example 9

Electrophoresis is run in 6% acrylamide gel having an ionic strength of 1X TBE at a temperature of 50° C. A continuous electric field of 2000 Volts is applied for 4.4 hours. This is followed in several runs using the following pulse sequences: sequence of pulses of 2 milliseconds at 2000 Volts alternating with 1 millisecond at −620 Volts; a sequence of 2 milliseconds at 2000 Volts alternating with 2 milliseconds at −620 Volts; and a sequence of 2 millisecond at 2000 Volts alternating with 3 milliseconds at −620 Volts. The relative mobility of the fragments as compared to a 100 base fragment is reported in Table IX.

Example 10

Electrophoresis is run in 6% acrylamide gel having an ionic strength of 1X TBE at a temperature of 50° C. A continuous field of 2000 Volts is applied for 4.4 hours, followed by a pulsed field sequence of 1 millisecond at 2000 Volts alternating with 4 milliseconds at −630 Volts run for 40.8 hours. Relative mobility of the fragments to a 100 base fragment is reported in Table X.

TABLE I

| Base Number | Distance (mm) 1X TBE | Relative Mobility 1X TBE | Distance (mm) 0.5X TBE | Relative Mobility 0.5X TBE | Distance (mm) 1.5X TBE | Relative Mobility 1.5X TBE |
| --- | --- | --- | --- | --- | --- | --- |
| 755 | 97 | 0.191 | 111 | 0.218 | 81 | 0.159 |
| 720 | 100 | 0.197 | 113 | 0.222 | 83 | 8.163 |
| 680 | 103 | 0.203 | 118 | 0.228 | 86 | 9.169 |
| 454 | 131 | 0.258 | 143 | 0.281 | 119 | 0.233 |
| 425 | 139 | 0.274 | 149 | 0.293 | 126 | 0.247 |
| 401 | 144 | 0.284 | 156 | 9.306 | 132 | 0.259 |
| 371 | 153 | 0.302 | 165 | 0.324 | 141 | 0.278 |
| 350 | 161 | 0.318 | 173 | 0.340 | 149 | 0.292 |
| 335 | 167 | 0.329 | 179 | 0.352 | 156 | 0.306 |
| 300 | 184 | 0.363 | 97 | 0.387 | 173 | 0.339 |
| 260 | 210 | 0.414 | 221 | 0.434 | 200 | 0.392 |
| 250 | 217 | 0.428 | 228 | 0.448 | 208 | 0.408 |
| 240 | 226 | 0.446 | 236 | 0.464 | 216 | 0.424 |
| 230 | 234 | 0.462 | 244 | 0.479 | 225 | 0.441 |
| 220 | 241 | 0.475 | 252 | 0.495 | 235 | 0.461 |
| 210 | 252 | 0.497 | 262 | 0.515 | 244 | 0.478 |
| 200 | 261 | 0.515 | 272 | 0.534 | 255 | 0.500 |
| 190 | 273 | 0.538 | 284 | 0.558 | 267 | 0.524 |
| 180 | 288 | 0.568 | 298 | 0.585 | 281 | 0.561 |
| 170 | 302 | 0.596 | 311 | 0.611 | 295 | 0.578 |
| 160 | 316 | 0.623 | 325 | 0.639 | 310 | 0.608 |
| 150 | 332 | 0.655 | 341 | 0.670 | 327 | 0.641 |
| 140 | 348 | 0.586 | 357 | 0.701 | 344 | 0.675 |
| 130 | 367 | 0.724 | 376 | 0.739 | 365 | 0.716 |
| 120 | 387 | 0.763 | 98 | 0.782 | 389 | 0.763 |

TABLE I-continued

| Base Number | Distance (mm) 1X TBE | Relative Mobility 1X TBE | Distance (mm) 0.5X TBE | Relative Mobility 0.5X TBE | Distance (mm) 1.5X TBE | Relative Mobility 1.5X TBE |
|---|---|---|---|---|---|---|
| 110 | 408 | 0.806 | 420 | 0.825 | 414 | 0.812 |
| 100 | 435 | 0.858 | 449 | 0.882 | 445 | 0.873 |
| 90 | 467 | 0.921 | 481 | 0.945 | 480 | 0.941 |
| 80 | 507 | 1.000 | 509 | 1.000 | 510 | 1.000 |

TABLE II

| Base Number | Distance (mm) 4% gel | Distance (mm) 6% gel | Distance (mm) 8% gel | Distance (mm) 12% gel | Relative Mobility 4% | Relative Mobility 6% | Relative Mobility 8% | Relative Mobility 12% |
|---|---|---|---|---|---|---|---|---|
| 755 | 96 | 102 | 86 | 86 | 0.217 | 0.198 | 0.193 | 0.172 |
| 720 | 100 | 104 | 89 | 88 | 0.226 | 0.202 | 0.200 | 0.176 |
| 680 | 103 | 107 | 90 | 91 | 0.233 | 0.207 | 0.202 | 0.182 |
| 454 | 140 | 137 | 118 | 118 | 0.316 | 0.208 | 0.261 | 0.236 |
| 425 | 147 | 145 | 121 | 124 | 0.332 | 0.281 | 0.272 | 0.248 |
| 401 | 154 | 151 | 127 | 129 | 0.348 | 0.283 | 0.285 | 0.258 |
| 371 | 165 | 161 | 135 | 138 | 0.372 | 0.312 | 0.303 | 0.276 |
| 350 | 174 | 169 | 142 | 146 | 0.393 | 0.328 | 0.319 | 0.292 |
| 335 | 181 | 176 | 147 | 151 | 0.400 | 0.341 | 0.330 | 0.302 |
| 300 | 200 | 194 | 163 | 168 | 0.451 | 0.376 | 0.366 | 0.336 |
| 260 | 224 | 221 | 182 | 191 | 0.506 | 0.428 | 0.409 | 0.382 |
| 250 | 231 | 228 | 169 | 198 | 0.521 | 0.442 | 0.425 | 0.396 |
| 240 | 239 | 236 | 195 | 206 | 0.540 | 0.457 | 0.438 | 0.412 |
| 230 | 248 | 244 | 202 | 214 | 0.560 | 0.473 | 0.454 | 0.428 |
| 220 | 255 | 253 | 204 | 222 | 0.576 | 0.490 | 0.458 | 0.444 |
| 210 | 263 | 264 | 217 | 231 | 0.594 | 0.512 | 0.468 | 0.462 |
| 200 | 272 | 275 | 227 | 241 | 0.614 | 0.533 | 0.510 | 0.482 |
| 190 | 283 | 287 | 237 | 252 | 0.639 | 0.558 | 0.533 | 0.504 |
| 180 | 294 | 301 | 248 | 265 | 0.664 | 0.583 | 0.557 | 0.530 |
| 170 | 303 | 315 | 260 | 278 | 0.684 | 0.610 | 0.584 | 0.556 |
| 160 | 311 | 326 | 274 | 293 | 0.702 | 0.638 | 0.616 | 0.586 |
| 150 | 326 | 344 | 289 | 310 | 0.740 | 0.667 | 0.649 | 0.620 |
| 140 | 341 | 362 | 305 | 328 | 0.770 | 0.702 | 0.685 | 0.656 |
| 130 | 355 | 382 | 322 | 348 | 0.801 | 0.749 | 0.724 | 0.696 |
| 120 | 370 | 405 | 342 | 371 | 0.835 | 0.785 | 0.769 | 0.742 |
| 110 | 385 | 427 | 363 | 397 | 0.869 | 0.828 | 0.816 | 0.794 |
| 100 | 402 | 457 | 367 | 425 | 0.907 | 0.886 | 0.870 | 0.850 |
| 90 | 410 | 483 | 414 | 459 | 0.944 | 0.936 | 0.930 | 0.918 |
| 80 | 443 | 516 | 445 | 500 | 1.000 | 1.000 | 1.000 | 1.000 |

TABLE III

| Base Number | Distance (mm) 56° C. | Relative Mobility 56° C. | Distance (mm) 45° C. | Relative Mobility 45° C. | Distance (mm) 40° C. | Relative Mobility 40° C. | Distance (mm) 35° C. | Relative Mobility 35° C. | Distance (mm) 30° C. | Relative Mobility 30° C. |
|---|---|---|---|---|---|---|---|---|---|---|
| 755 | 96 | 0.191 | 95 | 0.187 | 100 | 0.196 | 93 | 0.185 | 94 | 0.195 |
| 720 | 97 | 0.183 | 98 | 0.193 | 103 | 0.202 | 95 | 0.188 | 97 | 0.201 |
| 680 | 101 | 0.201 | 101 | 0.199 | 107 | 0.210 | 98 | 0.194 | 100 | 0.207 |
| 454 | 133 | 0.265 | 132 | 0.260 | 143 | 0.281 | 131 | 0.260 | 139 | 0.288 |
| 425 | 140 | 0.279 | 138 | 0.272 | 150 | 0.295 | 137 | 0.272 | 148 | 0.307 |
| 401 | 147 | 0.293 | 144 | 0.283 | 158 | 0.310 | 143 | 0.284 | 155 | 0.322 |
| 371 | 156 | 0.311 | 153 | 0.301 | 189 | 0.332 | 154 | 0.308 | 165 | 0.342 |
| 350 | 165 | 0.829 | 161 | 0.317 | 178 | 0.350 | 160 | 0.317 | 173 | 0.359 |
| 335 | 171 | 0.341 | 167 | 0.329 | 184 | 0.361 | 166 | 0.320 | 179 | 0.371 |
| 300 | 188 | 0.375 | 184 | 0.362 | 202 | 0.397 | 183 | 0.363 | 195 | 0.405 |
| 260 | 211 | 0.420 | 210 | 0.413 | 228 | 0.448 | 209 | 0.415 | 220 | 0.458 |
| 250 | 219 | 0.436 | 216 | 0.425 | 235 | 0.462 | 215 | 0.427 | 228 | 0.469 |
| 240 | 228 | 0.450 | 225 | 0.443 | 240 | 0.472 | 223 | 0.442 | 235 | 0.488 |
| 230 | 234 | 0.466 | 233 | 0.459 | 254 | 0.499 | 231 | 0.458 | 243 | 0.504 |
| 220 | 244 | 0.486 | 241 | 0.474 | 262 | 0.515 | 241 | 0.471 | 253 | 0.525 |
| 210 | 253 | 0.504 | 250 | 0.492 | 273 | 0.536 | 249 | 0.494 | 262 | 0.544 |
| 200 | 263 | 0.524 | 261 | 0.514 | 282 | 0.554 | 260 | 0.516 | 272 | 0.564 |
| 190 | 275 | 0.548 | 272 | 0.535 | 284 | 0.578 | 271 | 0.538 | 282 | 0.585 |
| 180 | 288 | 0.574 | 285 | 0.581 | 305 | 0.599 | 284 | 0.583 | 292 | 0.606 |
| 170 | 300 | 0.598 | 299 | 0.589 | 317 | 0.623 | 296 | 0.591 | 303 | 0.629 |
| 160 | 315 | 0.827 | 313 | 0.616 | 329 | 0.646 | 312 | 0.619 | 315 | 0.654 |
| 150 | 332 | 0.661 | 329 | 0.648 | 343 | 0.674 | 328 | 0.651 | 327 | 0.678 |
| 140 | 350 | 0.497 | 345 | 0.679 | 360 | 0.747 | 345 | 0.685 | 341 | 0.707 |
| 130 | 379 | 0.737 | 363 | 0.715 | 380 | 0.747 | 363 | 0.720 | 358 | 0.743 |
| 120 | 392 | 0.781 | 385 | 0.758 | 402 | 0.790 | 385 | 0.764 | 377 | 0.782 |
| 110 | 415 | 0.827 | 409 | 0.805 | 427 | 0.839 | 409 | 0.812 | 393 | 0.828 |
| 100 | 440 | 0.874 | 440 | 0.866 | 453 | 0.890 | 437 | 0.867 | 424 | 0.880 |
| 90 | 470 | 0.936 | 475 | 0.935 | 482 | 0.947 | 470 | 0.933 | 452 | 0.938 |
| 80 | 502 | 1.000 | 508 | 1.000 | 509 | 1.000 | 504 | 1.000 | 482 | 1.000 |

TABLE IV

| Base Number | Distance (mm) 500 V | Distance (mm) 750 V | Distance (mm) 1000 V | Distance (mm) 1500 V | Distance (mm) 2000 V | Distance (mm) 2500 V | Distance (mm) 3000 V | Distance (mm) 4000 V | Distance (mm) 5000 V |
|---|---|---|---|---|---|---|---|---|---|
| 755 | 55 | 74 | 89 | 98 | 102 | 119 | 128 | 121 | 133 |
| 720 | 58 | 77 | 92 | 101 | 104 | 121 | 131 | 124 | 136 |
| 680 | 62 | 81 | 96 | 105 | 107 | 123 | 134 | 128 | 138 |
| 590 | 74 | 93 | 106 | 116 | 117 | 133 | 144 | 135 | 146 |
| 527 | 86 | 103 | 117 | 127 | 124 | 141 | 153 | 141 | 153 |
| 454 | 102 | 119 | 132 | 144 | 137 | 154 | 169 | 153 | 168 |
| 401 | 118 | 133 | 147 | 161 | 151 | 169 | 185 | 165 | 179 |
| 271 | 130 | 143 | 158 | 172 | 169 | 179 | 195 | 173 | 188 |
| 350 | 135 | 152 | 167 | 181 | 176 | 188 | 203 | 182 | 195 |
| 325 | 147 | 158 | 173 | 188 | 194 | 194 | 210 | 188 | 202 |
| 300 | 167 | 177 | 193 | 203 | 221 | 213 | 229 | 205 | 217 |
| 260 | 196 | 204 | 220 | 236 | 228 | 237 | 255 | 227 | 240 |
| 250 | 204 | 213 | 227 | 245 | 236 | 244 | 283 | 234 | 248 |
| 240 | 212 | 220 | 235 | 254 | 244 | 252 | 270 | 242 | 253 |
| 230 | 222 | 229 | 244 | 262 | 253 | 261 | 279 | 249 | 262 |
| 220 | 232 | 238 | 253 | 271 | 264 | 272 | 290 | 258 | 270 |
| 210 | 243 | 246 | 263 | 282 | 275 | 281 | 299 | 267 | 290 |
| 200 | 255 | 258 | 276 | 292 | 287 | 203 | 309 | 278 | 291 |
| 190 | 267 | 271 | 287 | 314 | 301 | 305 | 319 | 289 | 302 |
| 180 | 280 | 284 | 300 | 327 | 315 | 318 | 331 | 302 | 315 |
| 170 | 293 | 298 | 312 | 341 | 326 | 331 | 344 | 314 | 329 |
| 160 | 307 | 313 | 327 | 355 | 344 | 346 | 359 | 328 | 342 |
| 150 | 321 | 330 | 343 | 373 | 362 | 362 | 375 | 343 | 358 |
| 140 | 337 | 347 | 359 | 394 | 382 | 380 | 394 | 359 | 374 |
| 130 | 356 | 366 | 378 | 416 | 405 | 399 | 413 | 376 | 393 |
| 120 | 378 | 388 | 400 | 441 | 427 | 424 | 437 | 398 | 418 |
| 110 | 401 | 412 | 424 | 467 | 457 | 448 | 463 | 422 | 442 |
| 100 | 429 | 439 | 453 | 496 | 438 | 477 | 490 | 450 | 470 |
| 90 | 461 | 466 | 482 | | | 507 | 519 | 482 | 503 |

| Base Number | Rel. Mob. 500 V | Rel. Mob. 750 V | Rel. Mob. 1000 V | Rel. Mob. 1500 V | Rel. Mob. 2000 V | Rel. Mob. 2500 V | Rel. Mob. 3000 V | Rel. Mob. 4000 V | Rel. Mob. 5000 V |
|---|---|---|---|---|---|---|---|---|---|
| 755 | 0.119 | 0.158 | 0.185 | 0.198 | 0.211 | 0.235 | 0.247 | 0.251 | 0.264 |
| 720 | 0.126 | 0.165 | 0.191 | 0.204 | 0.215 | 0.239 | 0.252 | 0.257 | 0.268 |
| 680 | 0.134 | 0.174 | 0.199 | 0.212 | 0.222 | 0.243 | 0.258 | 0.261 | 0.274 |
| 590 | 0.161 | 0.200 | 0.220 | 0.234 | 0.242 | 0.262 | 0.277 | 0.280 | 0.290 |
| 527 | 0.187 | 0.221 | 0.243 | 0.256 | 0.257 | 0.278 | 0.295 | 0.293 | 0.304 |
| 454 | 0.221 | 0.255 | 0.274 | 0.290 | 0.284 | 0.304 | 0.326 | 0.317 | 0.330 |
| 401 | 0.256 | 0.285 | 0.305 | 0.325 | 0.313 | 0.333 | 0.356 | 0.342 | 0.356 |
| 271 | 0.282 | 0.307 | 0.328 | 0.347 | 0.333 | 0.353 | 0.376 | 0.359 | 0.374 |
| 350 | 0.302 | 0.326 | 0.346 | 0.365 | 0.350 | 0.371 | 0.381 | 0.376 | 0.384 |
| 325 | 0.319 | 0.339 | 0.359 | 0.379 | 0.364 | 0.383 | 0.405 | 0.390 | 0.402 |
| 300 | 0.362 | 0.360 | 0.400 | 0.419 | 0.402 | 0.420 | 0.441 | 0.425 | 0.431 |
| 260 | 0.425 | 0.438 | 0.456 | 0.476 | 0.458 | 0.467 | 0.491 | 0.471 | 0.477 |
| 250 | 0.443 | 0.457 | 0.471 | 0.494 | 0.472 | 0.481 | 0.507 | 0.485 | 0.489 |
| 240 | 0.460 | 0.472 | 0.488 | 0.512 | 0.489 | 0.497 | 0.520 | 0.502 | 0.503 |
| 230 | 0.482 | 0.491 | 0.508 | 0.528 | 0.505 | 0.515 | 0.538 | 0.517 | 0.521 |
| 220 | 0.503 | 0.511 | 0.525 | 0.546 | 0.524 | 0.536 | 0.559 | 0.535 | 0.537 |
| 210 | 0.527 | 0.532 | 0.546 | 0.569 | 0.547 | 0.554 | 0.576 | 0.554 | 0.567 |
| 200 | 0.553 | 0.554 | 0.568 | 0.589 | 0.569 | 0.578 | 0.595 | 0.577 | 0.579 |
| 190 | 0.579 | 0.582 | 0.595 | 0.600 | 0.594 | 0.602 | 0.615 | 0.600 | 0.600 |
| 180 | 0.607 | 0.609 | 0.622 | 0.633 | 0.623 | 0.627 | 0.638 | 0.627 | 0.626 |
| 170 | 0.636 | 0.639 | 0.647 | 0.659 | 0.652 | 0.653 | 0.663 | 0.651 | 0.654 |
| 160 | 0.666 | 0.672 | 0.678 | 0.688 | 0.679 | 0.882 | 0.692 | 0.680 | 0.680 |
| 150 | 0.696 | 0.708 | 0.712 | 0.716 | 0.712 | 0.714 | 0.723 | 0.712 | 0.712 |
| 140 | 0.731 | 0.745 | 0.745 | 0.752 | 0.749 | 0.750 | 0.759 | 0.745 | 0.744 |
| 130 | 0.772 | 0.785 | 0.784 | 0.794 | 0.791 | 0.787 | 0.798 | 0.784 | 0.781 |
| 120 | 0.820 | 0.833 | 0.830 | 0.839 | 0.839 | 0.836 | 0.842 | 0.826 | 0.827 |
| 110 | 0.870 | 0.884 | 0.880 | 0.889 | 0.884 | 0.894 | 0.892 | 0.876 | 0.879 |
| 100 | 0.931 | 0.942 | 0.948 | 0.942 | 0.946 | 0.941 | 0.944 | 0.934 | 0.934 |
| 90 | 1.000 | 1.000 | 1.000 | 1.000 | 1.000 | 1.000 | 1.000 | 1.000 | 1.000 |

TABLE V

| Base Number | Constant Field Distance (mm) 2000 V | Distance (mm) 1 s 1000 V; 1 s OV | Distance (mm) 1 s 1000 V; 2 s OV | Distance (mm) 1 s 1000 V; 5 s OV | Constant Field Relative Mobility 2000 V | Relative Mobility 1 s 1000 V; 1 s OV | Relative Mobility 1 s 1000 V; 2 s OV | Relative Mobility 1 s 1000 V; 5 s OV |
|---|---|---|---|---|---|---|---|---|
| 755 | 66 | 78 | 62 | 55 | 0.136 | 0.153 | 0.129 | 0.115 |
| 720 | 69 | 81 | 65 | 57 | 0.142 | 0.159 | 0.135 | 0.119 |
| 680 | 73 | 85 | 69 | 59 | 0.150 | 0.167 | 0.143 | 0.123 |
| 590 | 83 | 97 | 79 | 67 | 0.170 | 0.190 | 0.163 | 0.141 |
| 527 | 94 | 109 | 90 | 76 | 0.193 | 0.214 | 0.187 | 0.159 |
| 454 | 109 | 127 | 108 | 93 | 0.224 | 0.249 | 0.224 | 0.195 |
| 425 | 117 | 135 | 117 | 101 | 0.240 | 0.265 | 0.248 | 0.211 |

TABLE V-continued

| Base Number | Constant Field Distance (mm) 2000 V | Distance (mm) 1 s 1000 V; 1 s OV | Distance (mm) 1 s 1000 V; 2 s OV | Distance (mm) 1 s 1000 V; 5 s OV | Constant Field Relative Mobility 2000 V | Relative Mobility 1 s 1000 V; 1 s OV | Relative Mobility 1 s 1000 V; 2 s OV | Relative Mobility 1 s 1000 V; 5 s OV |
|---|---|---|---|---|---|---|---|---|
| 401 | 124 | 143 | 125 | 109 | 0.255 | 0.280 | 0.258 | 0.228 |
| 371 | 134 | 155 | 137 | 119 | 0.275 | 0.304 | 0.284 | 0.249 |
| 350 | 142 | 164 | 146 | 128 | 0.292 | 0.322 | 0.303 | 0.268 |
| 335 | 140 | 170 | 153 | 134 | 0.306 | 0.333 | 0.317 | 0.280 |
| 300 | 167 | 189 | 172 | 154 | 0.343 | 0.371 | 0.357 | 0.322 |
| 260 | 194 | 215 | 200 | 181 | 0.398 | 0.422 | 0.415 | 0.379 |
| 250 | 202 | 223 | 207 | 189 | 0.415 | 0.437 | 0.428 | 0.395 |
| 240 | 210 | 232 | 212 | 197 | 0.431 | 0.455 | 0.440 | 0.412 |
| 230 | 219 | 241 | 226 | 207 | 0.450 | 0.473 | 0.489 | 0.433 |
| 220 | 229 | 251 | 236 | 218 | 0.470 | 0.492 | 0.498 | 0.456 |
| 210 | 238 | 261 | 246 | 227 | 0.489 | 0.512 | 0.518 | 0.475 |
| 200 | 249 | 272 | 257 | 240 | 0.511 | 0.533 | 0.533 | 0.502 |
| 190 | 261 | 284 | 268 | 254 | 0.536 | 0.557 | 0.556 | 0.531 |
| 180 | 275 | 297 | 281 | 266 | 0.565 | 0.582 | 0.583 | 0.558 |
| 170 | 289 | 310 | 294 | 280 | 0.593 | 0.608 | 0.610 | 0.586 |
| 160 | 304 | 326 | 305 | 295 | 0.624 | 0.639 | 0.633 | 0.617 |
| 150 | 320 | 343 | 320 | 309 | 0.657 | 0.673 | 0.664 | 0.646 |
| 140 | 338 | 361 | 335 | 323 | 0.694 | 0.708 | 0.695 | 0.676 |
| 130 | 358 | 381 | 351 | 341 | 0.735 | 0.747 | 0.728 | 0.713 |
| 120 | 379 | 402 | 372 | 362 | 0.778 | 0.788 | 0.772 | 0.757 |
| 110 | 401 | 425 | 394 | 384 | 0.823 | 0.833 | 0.817 | 0.803 |
| 100 | 426 | 451 | 419 | 412 | 0.875 | 0.884 | 0.868 | 0.862 |
| 90 | 455 | 483 | 450 | 442 | 0.934 | 0.941 | 0.934 | 0.925 |
| 80 | 487 | 510 | 482 | 478 | 1.000 | 1.000 | 1.000 | 1.000 |

TABLE VI

| Base Number | Constant Field Distance (mm) 2000 V/4.4 hrs. | Distance (mm) 1 s 2 KV; 1 s −300 V | Distance (mm) 1 s 2 KV; 1 s −620 V | Distance (mm) 1 s 2 KV; 4 s −630 V | Distance (mm) 2 s 2 KV; 2 s −1000 V | Distance (mm) 2 s KV; 1 s −2 kV | Constant Field Relative Mobility 2000 V/ 4.4 hrs. |
|---|---|---|---|---|---|---|---|
| 755 | 110 | 73 | 70 | 68 | 73 | 80 | 0.225 |
| 720 | 113 | 76 | 74 | 72 | 79 | 86 | 0.232 |
| 680 | 117 | 80 | 78 | 77 | 83 | 91 | 0.240 |
| 590 | 127 | 90 | 92 | 94 | 98 | 106 | 0.260 |
| 527 | 136 | 98 | 104 | 108 | 111 | 121 | 0.279 |
| 454 | 154 | 113 | 119 | 131 | 132 | 142 | 0.316 |
| 425 | 162 | 120 | 127 | 141 | 142 | 152 | 0.332 |
| 401 | 170 | 127 | 136 | 151 | 152 | 162 | 0.348 |
| 371 | 182 | 136 | 144 | 164 | 162 | 176 | 0.373 |
| 350 | 190 | 144 | 155 | 174 | 174 | 185 | 0.389 |
| 335 | 197 | 149 | 141 | 183 | 182 | 194 | 0.404 |
| 300 | 217 | 166 | 182 | 204 | 204 | 216 | 0.445 |
| 260 | 247 | 191 | 211 | 238 | 235 | 249 | 0.506 |
| 250 | 254 | 198 | 219 | 246 | 243 | 259 | 0.520 |
| 240 | 263 | 206 | 228 | 256 | 252 | 266 | 0.539 |
| 230 | 273 | 213 | 237 | 267 | 262 | 278 | 0.559 |
| 220 | 282 | 222 | 248 | 277 | 273 | 288 | 0.578 |
| 210 | 292 | 230 | 257 | 288 | 283 | 298 | 0.598 |
| 200 | 302 | 240 | 268 | 299 | 294 | 309 | 0.619 |
| 190 | 314 | 250 | 282 | 310 | 305 | 321 | 0.643 |
| 180 | 326 | 260 | 296 | 323 | 316 | 334 | 0.672 |
| 170 | 341 | 273 | 312 | 337 | 331 | 347 | 0.699 |
| 160 | 355 | 287 | 327 | 351 | 344 | 364 | 0.727 |
| 150 | 374 | 302 | 344 | 370 | 361 | 383 | 0.766 |
| 140 | 394 | 317 | 362 | 390 | 380 | 404 | 0.807 |
| 130 | 417 | 335 | 381 | 415 | 402 | 427 | 0.855 |
| 120 | 441 | 353 | 404 | 442 | 426 | 455 | 0.904 |
| 110 | 485 | 371 | 430 | 470 | 453 | 481 | 0.953 |
| 100 | 488 | 393 | 461 | 490 | 481 | 507 | 1.000 |

| Base Number | Relative Mobility 1 s 2 KV; 1 s −300 V | Relative Mobility 1 s 2 KV; 1 s −620 V | Relative Mobility 1 s 2 KV; 4 s −630 V | Relative Mobility 2 s 2 KV; 2 s −1000 V | Relative Mobility 2 s KV; 1 s −2 KV |
|---|---|---|---|---|---|
| 755 | 0.166 | 0.152 | 0.136 | 0.152 | 0.158 |
| 720 | 0.193 | 0.161 | 0.144 | 0.164 | 0.170 |
| 680 | 0.204 | 0.169 | 0.154 | 0.173 | 0.179 |
| 590 | 0.226 | 0.200 | 0.188 | 0.204 | 0.209 |
| 527 | 0.249 | 0.226 | 0.216 | 0.231 | 0.239 |
| 454 | 0.288 | 0.258 | 0.263 | 0.274 | 0.280 |
| 425 | 0.305 | 0.275 | 0.283 | 0.295 | 0.300 |
| 401 | 0.323 | 0.293 | 0.303 | 0.316 | 0.320 |

TABLE VI-continued

| | | | | | |
|---|---|---|---|---|---|
| 371 | 0.346 | 0.312 | 0.329 | 0.337 | 0.347 |
| 350 | 0.368 | 0.336 | 0.349 | 0.362 | 0.365 |
| 335 | 0.379 | 0.349 | 0.367 | 0.378 | 0.383 |
| 300 | 0.422 | 0.395 | 0.409 | 0.424 | 0.426 |
| 260 | 0.486 | 0.458 | 0.477 | 0.489 | 0.491 |
| 250 | 0.504 | 0.475 | 0.493 | 0.505 | 0.511 |
| 240 | 0.524 | 0.495 | 0.513 | 0.524 | 0.529 |
| 230 | 0.542 | 0.514 | 0.535 | 0.545 | 0.548 |
| 220 | 0.585 | 0.536 | 0.555 | 0.568 | 0.568 |
| 210 | 0.585 | 0.557 | 0.577 | 0.586 | 0.588 |
| 200 | 0.611 | 0.581 | 0.599 | 0.611 | 0.609 |
| 190 | 0.636 | 0.612 | 0.621 | 0.634 | 0.633 |
| 180 | 0.662 | 0.642 | 0.647 | 0.661 | 0.650 |
| 170 | 0.695 | 0.677 | 0.675 | 0.686 | 0.684 |
| 160 | 0.730 | 0.709 | 0.703 | 0.715 | 0.718 |
| 150 | 0.768 | 0.746 | 0.741 | 0.751 | 0.755 |
| 140 | 0.807 | 0.785 | 0.782 | 0.790 | 0.797 |
| 130 | 0.862 | 0.826 | 0.832 | 0.836 | 0.842 |
| 120 | 0.897 | 0.876 | 0.886 | 0.886 | 0.897 |
| 110 | 0.944 | 0.933 | 0.942 | 0.942 | 0.949 |
| 100 | 1.000 | 1.000 | 1.000 | 1.000 | 1.000 |

TABLE VII

| Base Number | Constant Field Distance (mm) 2000 V | Distance (mm) 1 ms 2 KV; 1 ms −300 V | Distance (mm) 2 ms 2 KV; 2 ms −300 V | Distance (mm) 2 ms 2KV; 4 ms −300 V | Constant Field Relative Mobility 2000 V | Relative Mobility 1 ms 2 KV; 1 ms −300 V | Relative Mobility 2 ms 2 KV; 2 ms −300 V | Relative Mobility 2 ms 2 KV; 4 ms −300 V |
|---|---|---|---|---|---|---|---|---|
| 755 | 110 | 73 | 82 | 80 | 0.225 | 0.166 | 0.176 | 0.172 |
| 720 | 113 | 76 | 86 | 85 | 0.232 | 0.193 | 0.184 | 0.182 |
| 680 | 117 | 80 | 91 | 89 | 0.240 | 0.204 | 0.195 | 0.191 |
| 590 | 127 | 90 | 106 | 103 | 0.260 | 0.229 | 0.227 | 0.221 |
| 527 | 136 | 93 | 118 | 117 | 0.279 | 0.249 | 0.263 | 0.251 |
| 454 | 154 | 113 | 137 | 136 | 0.316 | 0.288 | 0.293 | 0.292 |
| 425 | 162 | 120 | 148 | 146 | 0.332 | 0.305 | 0.313 | 0.313 |
| 401 | 170 | 127 | 155 | 155 | 0.348 | 0.323 | 0.332 | 0.333 |
| 371 | 182 | 136 | 164 | 169 | 0.373 | 0.346 | 0.351 | 0.363 |
| 350 | 190 | 144 | 177 | 177 | 0.389 | 0.366 | 0.379 | 0.380 |
| 335 | 192 | 149 | 184 | 185 | 0.393 | 0.379 | 0.394 | 0.397 |
| 300 | 217 | 166 | 203 | 206 | 0.445 | 0.422 | 0.435 | 0.442 |
| 260 | 247 | 191 | 233 | 235 | 0.506 | 0.466 | 0.498 | 0.504 |
| 250 | 254 | 198 | 241 | 242 | 0.520 | 0.504 | 0.516 | 0.519 |
| 240 | 263 | 206 | 250 | 251 | 0.539 | 0.524 | 0.535 | 0.539 |
| 230 | 273 | 213 | 260 | 261 | 0.559 | 0.542 | 0.557 | 0.560 |
| 220 | 282 | 222 | 270 | 270 | 0.578 | 0.565 | 0.576 | 0.579 |
| 210 | 292 | 230 | 280 | 280 | 0.598 | 0.585 | 0.600 | 0.601 |
| 200 | 302 | 240 | 290 | 291 | 0.619 | 0.611 | 0.621 | 0.624 |
| 190 | 314 | 250 | 301 | 302 | 0.643 | 0.636 | 0.645 | 0.648 |
| 180 | 326 | 260 | 314 | 314 | 0.672 | 0.662 | 0.672 | 0.674 |
| 170 | 341 | 273 | 326 | 326 | 0.699 | 0.695 | 0.698 | 0.700 |
| 180 | 355 | 287 | 338 | 339 | 0.727 | 0.730 | 0.724 | 0.727 |
| 150 | 374 | 302 | 354 | 354 | 0.766 | 0.768 | 0.758 | 0.760 |
| 140 | 394 | 317 | 372 | 371 | 0.807 | 0.807 | 0.797 | 0.796 |
| 130 | 417 | 335 | 394 | 392 | 0.855 | 0.852 | 0.844 | 0.841 |
| 120 | 441 | 353 | 417 | 415 | 0.904 | 0.898 | 0.893 | 0.891 |
| 110 | 465 | 371 | 440 | 440 | 0.953 | 0.944 | 0.942 | 0.944 |
| 100 | 483 | 393 | 467 | 466 | 1.000 | 1.000 | 1.000 | 1.000 |

TABLE VIII

| Base Number | Constant Field Distance (mm) 2000 V/4 hrs. | Distance (mm) 1 s 2 KV; 1 s −620 V | Distance (mm) 10 ms 2 KV; 10 ms −620 V | Distance (mm) 5 ms 2 KV; 5 ms −620 V | Distance (mm) 2 ms 2 KV; 2 ms −620 V | Distance (mm) 1 ms 2 KV; 1 ms −620 V | Constant Field Relative Mobility 2000 V/4 hrs. |
|---|---|---|---|---|---|---|---|
| 755 | 104 | 116 | 114 | 90 | 84 | 70 | 0.240 |
| 720 | 106 | 122 | 118 | 94 | 89 | 74 | 0.245 |
| 680 | 109 | 124 | 121 | 99 | 93 | 78 | 0.252 |
| 590 | 118 | 133 | 131 | 112 | 107 | 92 | 0.273 |
| 527 | 127 | 142 | 142 | 123 | 119 | 104 | 0.293 |
| 454 | 143 | 158 | 159 | 141 | 138 | 119 | 0.330 |
| 425 | 150 | 165 | 166 | 150 | 146 | 127 | 0.346 |
| 401 | 158 | 174 | 174 | 158 | 155 | 135 | 0.365 |
| 371 | 167 | 186 | 185 | 171 | 167 | 144 | 0.386 |
| 350 | 176 | 196 | 194 | 181 | 178 | 155 | 0.406 |
| 335 | 182 | 203 | 201 | 189 | 186 | 161 | 0.420 |
| 300 | 200 | 223 | 221 | 210 | 209 | 182 | 0.462 |
| 260 | 225 | 253 | 251 | 239 | 239 | 211 | 0.520 |

TABLE VIII-continued

| | | | | | | | | |
|---|---|---|---|---|---|---|---|---|
| 250 | 233 | 260 | 260 | 247 | 249 | 219 | 0.538 | |
| 240 | 241 | 271 | 270 | 257 | 257 | 228 | 0.557 | |
| 230 | 249 | 281 | 280 | 267 | 268 | 237 | 0.575 | |
| 220 | 259 | 293 | 290 | 278 | 280 | 246 | 0.598 | |
| 210 | 269 | 305 | 301 | 289 | 292 | 257 | 0.621 | |
| 200 | 280 | 318 | 314 | 301 | 305 | 268 | 0.647 | |
| 190 | 293 | 331 | 328 | 314 | 319 | 282 | 0.677 | |
| 180 | 305 | 345 | 344 | 328 | 333 | 296 | 0.704 | |
| 170 | 319 | 360 | 360 | 343 | 349 | 310 | 0.737 | |
| 160 | 334 | 377 | 376 | 358 | 365 | 323 | 0.771 | |
| 150 | 351 | 396 | 395 | 377 | 383 | 340 | 0.811 | |
| 140 | 369 | 416 | 415 | 396 | 403 | 358 | 0.852 | |
| 130 | 389 | 443 | 440 | 419 | 425 | 378 | 0.898 | |
| 120 | 410 | 470 | 466 | 449 | 454 | 400 | 0.947 | |
| 110 | 433 | 500 | 495 | 479 | 483 | 426 | 1.000 | |

| Base Number | Relative Mobility 1 s 2 KV; 1 s −620 V | Relative Mobility 10 ms 2 KV; 10 ms −620 V | Relative Mobility 5 ms 2 KV; 5 ms −620 V | Relative Mobility 2 ms 2 KV; 2 ms −620 V | Relative Mobility 1 ms 2 KV; 1 ms −620 V |
|---|---|---|---|---|---|
| 755 | 0.236 | 0.230 | 0.188 | 0.174 | 0.164 |
| 720 | 0.244 | 0.238 | 0.196 | 0.184 | 0.174 |
| 680 | 0.248 | 0.244 | 0.207 | 0.193 | 0.183 |
| 590 | 0.266 | 0.265 | 0.234 | 0.222 | 0.216 |
| 527 | 0.284 | 0.287 | 0.257 | 0.246 | 0.244 |
| 454 | 0.316 | 0.321 | 0.294 | 0.286 | 0.279 |
| 425 | 0.330 | 0.335 | 0.313 | 0.302 | 0.298 |
| 401 | 0.346 | 0.352 | 0.330 | 0.321 | 0.317 |
| 371 | 0.372 | 0.374 | 0.357 | 0.346 | 0.338 |
| 350 | 0.392 | 0.392 | 0.378 | 0.369 | 0.364 |
| 335 | 0.406 | 0.406 | 0.395 | 0.385 | 0.378 |
| 300 | 0.446 | 0.446 | 0.438 | 0.433 | 0.427 |
| 260 | 0.506 | 0.507 | 0.499 | 0.495 | 0.495 |
| 250 | 0.520 | 0.525 | 0.516 | 0.516 | 0.514 |
| 240 | 0.542 | 0.545 | 0.537 | 0.532 | 0.535 |
| 230 | 0.562 | 0.566 | 0.557 | 0.555 | 0.556 |
| 220 | 0.586 | 0.586 | 0.580 | 0.580 | 0.582 |
| 210 | 0.610 | 0.606 | 0.603 | 0.605 | 0.603 |
| 200 | 0.636 | 0.634 | 0.628 | 0.631 | 0.629 |
| 190 | 0.662 | 0.663 | 0.656 | 0.660 | 0.662 |
| 180 | 0.690 | 0.695 | 0.685 | 0.689 | 0.695 |
| 170 | 0.720 | 0.727 | 0.716 | 0.723 | 0.726 |
| 160 | 0.754 | 0.760 | 0.747 | 0.756 | 0.758 |
| 150 | 0.792 | 0.798 | 0.787 | 0.793 | 0.798 |
| 140 | 0.836 | 0.838 | 0.827 | 0.834 | 0.840 |
| 130 | 0.886 | 0.889 | 0.875 | 0.880 | 0.887 |
| 120 | 0.940 | 0.941 | 0.937 | 0.940 | 0.939 |
| 110 | 1.000 | 1.000 | 1.000 | 1.000 | 1.000 |

TABLE IX

| Base Number | Constant Field Distance (mm) 2000 V/4.4 hrs. | Distance (mm) 2 ms 2 KV; 1 ms −620 V | Distance (mm) 2 ms 2 KV; 2 ms −620 V | Distance (mm) 2 ms 2 KV; 3 ms −620 V | Constant Field Relative Mobility 2000 V/4.4 hrs. | Relative Mobility 2 ms 2 KV; 1 ms −620 V | Relative Mobility 2 ms 2 KV; 2 ms −620 V | Relative Mobility 2 ms 2 KV; 3 ms −620 V |
|---|---|---|---|---|---|---|---|---|
| 755 | 110 | 86 | 84 | 73 | 0.225 | 0.183 | 0.165 | 0.151 |
| 720 | 113 | 91 | 89 | 77 | 0.232 | 0.194 | 0.175 | 0.160 |
| 680 | 117 | 94 | 93 | 82 | 0.240 | 0.200 | 0.183 | 0.170 |
| 590 | 127 | 107 | 107 | 94 | 0.260 | 0.228 | 0.210 | 0.195 |
| 527 | 136 | 119 | 118 | 107 | 0.279 | 0.253 | 0.232 | 0.222 |
| 454 | 154 | 140 | 138 | 124 | 0.316 | 0.298 | 0.271 | 0.257 |
| 425 | 162 | 149 | 146 | 133 | 0.332 | 0.317 | 0.287 | 0.276 |
| 401 | 170 | 158 | 155 | 141 | 0.348 | 0.336 | 0.305 | 0.293 |
| 371 | 182 | 169 | 167 | 154 | 0.373 | 0.360 | 0.328 | 0.320 |
| 350 | 190 | 179 | 178 | 161 | 0.389 | 0.381 | 0.350 | 0.334 |
| 335 | 192 | 186 | 196 | 169 | 0.393 | 0.396 | 0.365 | 0.351 |
| 300 | 217 | 206 | 209 | 190 | 0.445 | 0.438 | 0.411 | 0.394 |
| 260 | 247 | 234 | 239 | 218 | 0.506 | 0.498 | 0.470 | 0.452 |
| 250 | 254 | 243 | 249 | 227 | 0.520 | 0.517 | 0.489 | 0.471 |
| 240 | 263 | 251 | 257 | 236 | 0.539 | 0.534 | 0.505 | 0.490 |
| 230 | 273 | 260 | 268 | 245 | 0.559 | 0.553 | 0.527 | 0.508 |
| 220 | 282 | 271 | 280 | 255 | 0.578 | 0.577 | 0.550 | 0.529 |
| 210 | 292 | 280 | 292 | 266 | 0.598 | 0.596 | 0.574 | 0.552 |
| 200 | 302 | 292 | 305 | 279 | 0.619 | 0.621 | 0.599 | 0.579 |
| 190 | 314 | 303 | 310 | 292 | 0.643 | 0.645 | 0.627 | 0.606 |
| 180 | 326 | 311 | 333 | 306 | 0.672 | 0.642 | 0.654 | 0.635 |
| 170 | 341 | 331 | 349 | 321 | 0.699 | 0.704 | 0.696 | 0.656 |
| 160 | 355 | 341 | 365 | 338 | 0.727 | 0.726 | 0.717 | 0.701 |
| 150 | 374 | 362 | 383 | 354 | 0.766 | 0.770 | 0.752 | 0.734 |
| 140 | 394 | 380 | 403 | 373 | 0.807 | 0.809 | 0.792 | 0.774 |
| 130 | 417 | 399 | 425 | 395 | 0.855 | 0.849 | 0.835 | 0.820 |

TABLE IX-continued

| Base Number | Constant Field Distance (mm) 2000 V/4.4 hrs. | Distance (mm) 2 ms 2 KV; 1 ms −620 V | Distance (mm) 2 ms 2 KV; 2 ms −620 V | Distance (mm) 2 ms 2 KV; 3 ms −620 V | Constant Field Relative Mobility 2000 V/4.4 hrs. | Relative Mobility 2 ms 2 KV; 1 ms −620 V | Relative Mobility 2 ms 2 KV; 2 ms −620 V | Relative Mobility 2 ms 2 KV; 3 ms −620 V |
|---|---|---|---|---|---|---|---|---|
| 120 | 441 | 420 | 454 | 420 | 0.904 | 0.894 | 0.892 | 0.871 |
| 110 | 465 | 443 | 483 | 450 | 0.953 | 0.943 | 0.949 | 0.934 |
| 100 | 488 | 470 | 509 | 482 | 1.000 | 1.000 | 1.000 | 1.000 |

TABLE X

| Base Number | Constant Field Distance (mm) 2000 V/4.4 hrs. | Distance (mm) 2 ms 2 KV; 4 ms −630 V | Constant Field Relative Mobility 2000 V/4.4 hrs. | Relative Mobility 2 ms 2 KV; 4 ms −630 V |
|---|---|---|---|---|
| 755 | 110 | 68 | 0.225 | 0.136 |
| 720 | 113 | 72 | 0.232 | 0.144 |
| 600 | 117 | 77 | 0.240 | 0.154 |
| 590 | 127 | 94 | 0.260 | 0.188 |
| 527 | 136 | 108 | 0.279 | 0.216 |
| 454 | 154 | 131 | 0.316 | 0.263 |
| 425 | 162 | 141 | 0.332 | 0.283 |
| 401 | 170 | 151 | 0.348 | 0.303 |
| 371 | 182 | 164 | 0.373 | 0.329 |
| 350 | 190 | 174 | 0.389 | 0.349 |
| 335 | 196 | 183 | 0.402 | 0.367 |
| 300 | 217 | 204 | 0.445 | 0.409 |
| 260 | 247 | 238 | 0.506 | 0.477 |
| 250 | 254 | 246 | 0.520 | 0.493 |
| 240 | 263 | 256 | 0.539 | 0.513 |
| 230 | 273 | 267 | 0.559 | 0.535 |
| 220 | 282 | 277 | 0.578 | 0.555 |
| 210 | 292 | 288 | 0.598 | 0.577 |
| 200 | 302 | 299 | 0.619 | 0.599 |
| 190 | 314 | 310 | 0.643 | 0.621 |
| 180 | 328 | 323 | 0.672 | 0.647 |
| 170 | 341 | 337 | 0.699 | 0.675 |
| 160 | 355 | 351 | 0.727 | 0.703 |
| 150 | 374 | 370 | 0.766 | 0.741 |
| 148 | 394 | 390 | 0.807 | 0.782 |
| 130 | 417 | 415 | 0.855 | 0.832 |
| 120 | 441 | 442 | 0.904 | 0.886 |
| 110 | 465 | 470 | 0.953 | 0.942 |
| 100 | 488 | 499 | 1.000 | 1.000 |

What is claimed is:

1. A method of determining the base sequence of large single stranded nucleic acid fragments using gel electrophoresis, comprising:
    applying to a polyacrylamide gell a mixture of single stranded nucleic acid fragments wherein the migration rate of a single stranded nucleic acid fragment of n+1 bases is substantially the same as the migration rate of a single stranded nucleic acid fragment of n bases in a polyacrylamide gel under a constant electric field;
    retarding the migration create of the single stranded nucleic acid fragment of n+1 bases below the migration rate of the single stranded nucleic acid fragment of n bases by applying to the mixture of single stranded nucleic acid fragments a plurality of sequences of electric field pulses in one dimension to the gel, each of said sequences being comprises of a first pulse of a positive magnitude $V_1$ applied for a time period of $T_1$, and a second pulse of a negative magnitude $V_2$ applied for a time period $T_2$, wherein $t_1$ and $V_1$ are not the same as $T_2$ and $V_2$;
    and sequencing the single stranded nucleic acid fragments.

2. The method according to claim 1, wherein said retarding of the migration rate comprises decompressing bands of single stranded nucleic acid fragments on the gel, thereby increasing the number of readable nucleic acid fragments on the gel.

3. The method according to claim 1, further comprising reading sequence data with an automated sequencer having a chart recorder, wherein bands on the chart recorder are spatially separated so as to facilitate single stranded nucleic acid base sequence determination.

4. The method according to claim 1, wherein at least one of $T_1$ and $T_2$ is from about 100 microseconds to about 10 milliseconds.

5. The method according to claim 4, wherein a least one of $T_1$ and $T_2$ is from about 1 millisecond to about 5 milliseconds.

6. The method according to claim 5, wherein at least one of $T_1$ and $T_2$ is from about 2 millisecond to about 4 milliseconds.

7. The method according to claim 1, wherein the absolute value of at least one of $V_1$ and $V_2$ is greater than zero and less than 10,000 Volts.

8. The method according to claim 7, wherein the absolute value of at least one of $V_1$ and $V_2$ is from about 300 to about 5000 Volts.

9. The method according to claim 8, wherein the absolute value of at least one of $V_1$ and $V_2$ is about 2000 Volts.

10. The method according to claim 1, wherein $$\frac{T_1 V_1 + T_2 V_2}{T_1 + T_2}$$

is essentially zero.

11. The method according to claim 1, wherein the absolute value of $V_1$ is greater than or equal to the absolute value of $V_2$.

12. The method according to claim 11, wherein the absolute value of $V_1$ is greater than the absolute value of $V_2$.

13. The method of claim 1, wherein $T_1$ is less than 2 milliseconds, $T_2$ is less than 2 milliseconds, $V_1$ is greater than 1500 Volts and less than 2500 Volts, and $V_2$ is greater than $-400$ Volts and less than $-200$ Volts.

14. The method according to claim 1, wherein $T_1$ less than 2 milliseconds, $T_2$ is less than 2 milliseconds, $V_1$ is greater than 1500 Volts and less than 2500 Volts, and is greater than $-700$ Volts and less than $-600$ Volts.

15. The method according to claim 1, wherein $T_1$ is greater than 1 millisecond and less than 3 milliseconds, $T_2$ is greater than 3 milliseconds and less than 5 milliseconds, $V_1$ is greater than 1500 Volts and less than 2500 Volts, and $V_2$ is greater than $-700$ Volts and less than $-600$ Volts.

16. The method according to claim 1, wherein $T_1$ is greater than millisecond and less than 3 milliseconds, $T_2$ is greater than 1 millisecond and less than 2 milliseconds, $V_1$ is greater than 1500 Volts and less than 2500 Volts, and $V_2$ is greater than $-1500$ Volts and less than $-500$ Volts.

17. The method according to claim 1, where $T_1$ is greater than one millisecond and less than 3 milliseconds, $T_2$ is less than 2 milliseconds, $V_1$ is greater than 1500 Volts and less than 2500 Volts, and $V_2$ is greater than $-2500$ Volts and less than $-1500$ Volts.

18. The method according to claim 1, wherein n is greater than 300.

19. The method according to claim 18, wherein n is greater than 400.

20. The method according to claim 19, wherein n is greater than 500.

21. The method according to claim 20, wherein n is greater than 600.

22. The method according to claim further comprising applying continuous field gel electrophoresis prior to the application of said a plurality of sequences of electric field pulses to the gel.

23. The method according to claim further comprising repeating the application of said plurality of sequences.

24. The method according to claim 1, wherein at least one of the first pulse and the second pulse is comprised of a plurality of subpulses.

25. A method of determining the base sequence of large single stranded ucleic acid fragments using gel electrophoresis, comprising:
applying to a mixture of single stranded nucleic acid fragments, wherein the migration rate of a single stranded nucleic acid fragment of n bases is substantially the same as the migration rate of a single stranded nucleic acid fragment of $n+1$ bases in a polyacrylamide gel under a constant electric field, a plurality of sequences of electric field pulses in one dimension to the gel, each of said sequences being comprises of a first pulse of positive magnitude $V_1$ applied for a time period $T_1$, and a second pulse of a negative magnitude $V_2$ applied for a time period $T_2$, wherein $T_1$ and $V_1$ are not the same as $T_2$ and $V_2$, and said $T_2$ being of the appropriate duration to allow a fragment of $n+1$ bases to relax to the negative field pulse without allowing a fragment of n bases to relax to the negative field pulse thereby retarding the migration rate of a single stranded nucleic acid fragment of $n+1$ bases below the migration rate of a single stranded nucleic acid fragment of n bases.

* * * * *

UNITED STATES PATENT AND TRADEMARK OFFICE
CERTIFICATE OF CORRECTION

PATENT NO.  :   5,167,784

DATED       :   December 1, 1992

INVENTOR(S) :   Jaan Noolandi et al.

It is certified that error appears in the above-identified patent and that said Letters Patent is hereby corrected as shown below:

On the cover page, in section [75], add

--Chantal Turmel, Cote St. Luc, Canada; and Eric Brassard, Montreal, Canada.--

Signed and Sealed this

Twelfth Day of October, 1993

Attest:

BRUCE LEHMAN

*Attesting Officer*    *Commissioner of Patents and Trademarks*

UNITED STATES PATENT AND TRADEMARK OFFICE
CERTIFICATE OF CORRECTION

PATENT NO. : 5,167,784
DATED : December 1, 1992
INVENTOR(S) : Jaan NOOLANDI et al.

It is certified that error appears in the above-identified patent and that said Letters Patent is hereby corrected as shown below:

On the cover page, in section [54], change the title of the invention to read:

--SEQUENCING OF LARGE NUCLEIC ACID FRAGMENTS--

Signed and Sealed this

Twenty-third Day of November, 1993

Attest:

BRUCE LEHMAN

Attesting Officer

Commissioner of Patents and Trademarks